United States Patent [19]
McKee

[11] Patent Number: 5,218,626
[45] Date of Patent: Jun. 8, 1993

[54] SOLID STATE PHOTO SENSOR WITH ADJUSTABLE VIEWING MEANS

[75] Inventor: William J. McKee, Palo Alto, Calif.

[73] Assignee: Picker International, Inc., Cleveland, Ohio

[21] Appl. No.: 877,474

[22] Filed: May 1, 1992

[51] Int. Cl.$^5$ .............................................. H05G 1/64
[52] U.S. Cl. ...................................... 378/99; 378/98; 378/210
[58] Field of Search ........................... 378/99, 98, 210; 250/213 VT, 239, 366; 358/211

[56] References Cited

U.S. PATENT DOCUMENTS 5,067,142  11/1991  Gall et al. .............................. 378/99

Primary Examiner—David P. Porta
Assistant Examiner—Don Wong
Attorney, Agent, or Firm—Timothy B. Gurin

[57] ABSTRACT

An x-ray source propagates radiation across an examination gap onto a intensifier tube input screen. The output screen of the intensifier tube is viewed by a video camera. A sampling means is disposed between the intensifier output screen and the video camera. The sampling means views the intensifier output screen and converts the viewed image into an electronic control signal for the x-ray source. The sampling means includes a first block pivotally secured to a second block below a receiving hole in the first block. The blocks are adjustably biased in pivoting tension about a pivot below the receiving hole. A barrel is frictionally engaged in the receiving hole. One end of the barrel is angled on one side and cutout on the other side. A mirror is fixedly disposed on the angled side such that light propagating through the cutout is reflected through the central axis of the barrel to a photo diode fixedly disposed at the other end of the barrel. The sampling means is disposed such that the mirror is positioned to view the face of the intensifier output screen. The pivot provides a pivoting adjustment of the mirror viewing position along a first line perpendicular to the pivot. The receiving hole and barrel cooperate to provide rotatable adjustment about the central axis of the barrel.

9 Claims, 2 Drawing Sheets

SOLID STATE PHOTO SENSOR WITH ADJUSTABLE VIEWING MEANS

BACKGROUND OF THE INVENTION

The present invention relates to monitoring of x-ray exposures in medical diagnostic equipment. It finds application in conjunction with radiographic apparatus, such as fluoroscopic imaging systems, and will be described with particular reference thereto. However, it should be appreciated that the invention will also find application in conjunction with other equipment where precise adjustable positioning of a radiation or visible light detection means is desirable.

Fluoroscopic imaging systems include a continuous source of radiographic energy, such as an x-ray tube, which propagates radiation through an object to be imaged, such as a human patient, onto a screen of fluorescent material, the object to be imaged being disposed in a gap between the x-ray source and the fluorescent screen.

X-ray radiation passing through the imaged object is attenuated according to the density of the material through which it has passed. Radiation passing through dense material, such as bone, will be attenuated more than radiation of similar energy passing through less dense material, such as tissue. For uniformly intense radiation entering an object the radiation energy exiting the object is a reflection of the attenuation occurring within the object. Attenuated radiation impinging on the fluorescent screen is absorbed by the fluorescent material thereon and converted into a relatively low brightness visible light in proportion to the radiation energy impinging at each point thereon. This conversion results in a two dimensional light image of the object represented by a plurality of different intensities of visible light. This light image can be visualized by the human eye or captured onto photographic film, which is generally more sensitive to light than to x-ray. The brightness of the fluorescent screen is sufficient to expose film placed in direct contact with the screen, but the light output is generally too low for direct diagnostic visualization, photographing with a camera, or viewing with a television camera. In many applications, a device is needed that will convert the x-rays into light and intensify, or increase the brightness of, the light. An image intensifier tube is such a device.

The intensifier tube can be described as an evacuated glass bottle. The large area of the bottle forming the bottom of the bottle is the input screen, and the small area that forms the 'cap' on the bottle is the output screen. The input screen is comprised of two layers. The first layer which the x-ray beam encounters contains a fluorescent material. The fluorescent material absorbs the incident x-rays and converts a portion thereof into a low level visible light. The light is absorbed by an adjacent photo cathode layer, the second layer of the input screen. The absorption of light by the photo cathode layer results in the emission of low energy electrons into the evacuated bottle. The intensifier tube is connected to an electrical energy source that applies a relatively high bias voltage between the photo cathode and the output screen. The bias voltage accelerates the low energy electrons in the tube towards the output screen. A plurality of electrodes in the intensifier tube steer the electrons towards the output screen. The accelerated electrons, which are now at a relatively high kinetic energy potential, converge on and strike the output screen phosphor which converts the electrons energy into relatively bright flashes of light representative of the radiation image at the input of the intensifier tube.

The input end of a video camera is held in fixed relation to the output of the intensifier tube in order that the output image of the intensifier tube can be viewed by the camera input. The video camera is part of a closed circuit television system which provides a visual image on a television screen, representative of the radiation image detected at the input of the image intensifier.

In fluoroscopy, the patient is exposed to a relatively low intensity source of continuous or rapidly pulsed x-ray radiation so that the radiologist can dynamically view the operation of the internal body structure being imaged on the television screen. In practice a balance is made between minimizing patient exposure to x-ray radiation and the need to provide sufficient radiation to produce a quality diagnostic image. Some factors that will influence the amount of radiation to be delivered to a patient in a particular imaging sequence are; the path length the radiation will traverse within the patient and the attenuation of the radiation within patient structures being imaged. Preliminary selection of x-ray dose rate can be made on the basis of empirical data however, because path length and attenuation are patient dependent variables, the actual effect of x-ray dose selection is not known until the output image is viewed. Further, in some fluoroscopic imaging systems, the x-ray source, image intensifier, video camera and related components are contained within a movable gantry structure which allows the fluoroscopic system to be dynamically positioned about the patient. Also, the patient couch can be moved, relative to the x-ray source and image intensifier, during imaging operations to optimize the image view. If the gantry and/or patient couch is adjusted during imaging the image intensity may change due to fluctuations in the radiation path length or different radiation attenuation characteristics in different portions of the patient. Because the viewed image is capable of dynamically changing due to the reasons set forth above, it is desirable to provide a means to dynamically adjust the x-ray dose rate precisely to maintain the same image quality regardless of changing conditions.

One way to assure consistent image quality is to measure the x-ray dose rate after the x-rays have passed through the object to be imaged. A way to accomplish this is to introduce a light sampling means between the intensifier tube and the video camera. The light sampling means samples a portion of light and directs the sampled light to a sensing and control means which modifies the x-ray dose in response thereto.

One such sampling means is comprised of a pair of mirrors or prisms disposed on a mirror assembly, a light opaque cylindrical housing and a photomultiplier tube (PMT). For the purpose of description the central axis of the housing is vertically oriented. The housing bottom is open and the housing top is closed. A light input hole is disposed along one side of the housing approximately mid-way between the top and bottom. The centers of two evenly distributed threaded screw holes are disposed between the light input hole and the bottom of the housing. The PMT is a vacuum tube device having a light detection array, an input for accepting electrical biasing for the detection array and an electrical output from the detection array. The PMT is snugly received through the bottom of the housing and is oriented such that light propagating through the light input hole will fall on the light detection array. The mirror assembly includes first and second support arms which are adjustably engaged to the housing. The first support arm is secured to the housing, below the light input hole, by projecting two screws through two horizontally oriented oval slots in a first portion of the first arm and securing the screws into the threaded holes in the housing. The horizontally oriented oval slots provide limited rotational movement about a horizontal axis perpendicular to the central vertical axis of the housing. A second, vertically oriented, portion extends perpendicular from the first portion and outward from the housing. A third portion, having two threaded holes for mounting the second arm, extends further outward from the housing and upwards from the second portion. The second arm is secured to the first arm by projecting two screws through an upper circular hole and a lower horizontally oriented oval slot in a first portion of the second arm and into the threaded screw holes in the third portion of the first arm. The lower oval slot provides for rotational movement about a horizontal axis perpendicular to the axis described in conjunction with the two horizontally oriented oval holes of the first arm. A second portion of the second arm extends perpendicular to the third portion of the first arm transverse to the face of the light input hole.

The two mirrors are attached to the second arm such that light propagating upward from the vertically oriented image intensifier tube is reflected generally horizontally by the first mirror to the second mirror which in turn reflects the light at a right angle directly into light input hole.

To align the mirrors to detect light from a point on the output of the intensifier screen, an x-ray mask is disposed between the x-ray source and the intensifier tube input screen. The x-ray mask is a sheet of x-ray transmissive and x-ray opaque pattern portions which causes a known x-ray pattern to be disposed on the intensifier input screen when the x-ray source is engaged. The x-ray pattern striking the intensifier input screen results in a representative light pattern on the intensifier output screen. The above described sampling means is positioned adjacent the video camera such that the first mirror extends between the intensifier output screen and the video camera to sample light from the output of the intensifier tube. The screws projecting through the oval slots of the first arm are loosened to allow rotational adjustment of the first arm thereby resulting in adjustment of where the mirror views the intensifier output screen along a first line which is generally parallel to the second portion of the second arm. While monitoring the electrical output of the intensifier tube, the first arm is rotated until the electrical output of the PMT is optimized. While holding the first arm in its adjusted position the screws are tightened securing the first arm to the housing. Next, the screws projecting through the hole and oval slot in the second arm are loosened to allow rotational adjustment of the second arm thereby resulting in the mirror assembly being adjusted along a second line across the intensifier output screen. The second line is generally perpendicular to the first line. While monitoring the electrical output of the PMT, the second arm is adjusted until the PMT output voltage is maximized. While holding the second arm in its adjusted position the screws are tightened securing the second arm to the first arm. The adjustment of the first and second arms continues iteratively until the PMT voltage output is maximized; this being an indication that the mirrors are centered on the light image created by the x-ray mask.

One problem with using the above described assembly to aim the mirrors is that once the screws in the oval slots are loosened for adjustment the entire assembly is subject to shifting thereby not providing a mechanism for subsequent arm adjustments to progressively build upon prior arm adjustments. Therefore, the adjuster is faced with the possibility of having to begin the adjustment process anew every time the securing screws are loosened. Also, the adjuster may inadvertently vary the alignment before or during the tightening of the alignment screws. Because of the above described problems the alignment of the mirrors tends to be time consuming and tedious.

Another problem with the above assembly is that two pair of securing screws, one pair per arm, at a right angles to each other, require tightening before the assembly is secured. As the sampling means typically resides in a confined space, the tightening of two pairs of screws at right angles is physically difficult.

The present invention contemplates an x-ray sensor with adjustable viewing means which provides an improved adjustment means which overcomes the above-referenced problem and others.

SUMMARY OF THE INVENTION

Disadvantages of the prior art are reduced or overcome by use of light directing means and light receiving means secured in optical alignment to each other on an adjustment apparatus that can selectively aim the light directing and light receiving means to sample light from a select one of a plurality of locations.

An advantage of the present invention is that adjustment of the light directing means and the light receiving means is made easier because they are secured in optical alignment to each other.

Another advantage of the present invention is that it provides a mechanism for progressive positioning adjustment of the light directing means and light receiving means.

Another advantage of the present invention is that it provides for quick visual adjustment of the light sampling means.

Another advantage of the present invention is its reduced complexity.

Another advantage of the present invention is its reduced number of components.

BRIEF DESCRIPTION OF THE DRAWINGS

The invention may take form in various parts, arrangements of parts or sizes of part. The drawings are only for the purpose of illustrating the preferred embodiment and are not to be construed as limiting the invention.

DETAILED DESCRIPTION OF THE PREFERRED EMBODIMENT

Figure 1:
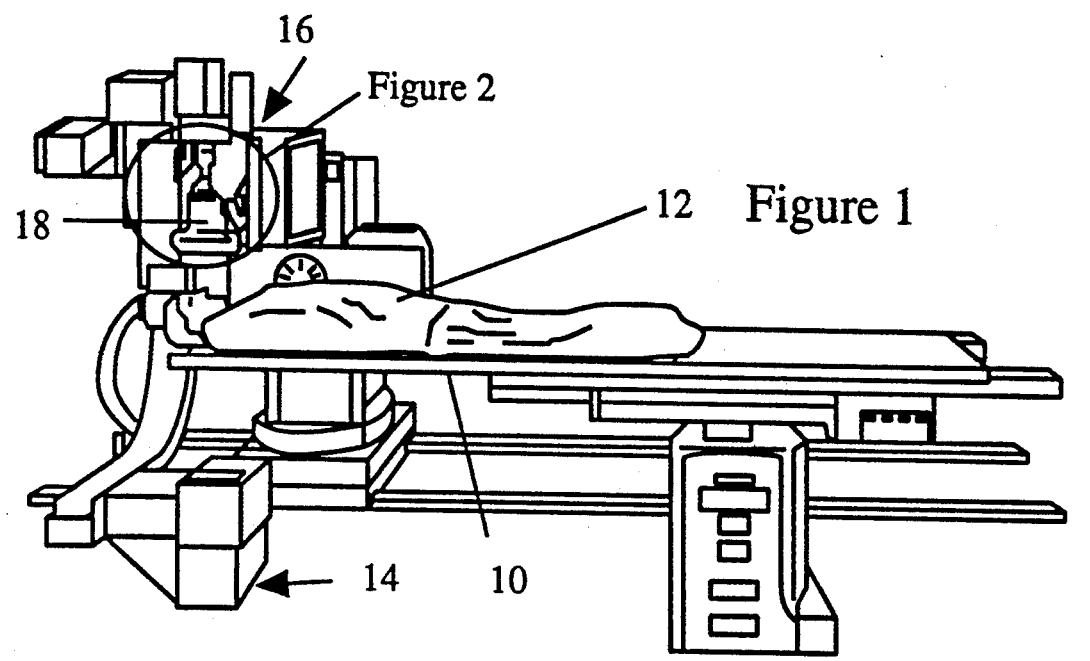
FIG. 1 is a perspective view of an exemplary x-ray system where the invention is used.

With reference to FIG. 1, a generally x-ray transparent patient table lo is selectively positioned to support a patient 12 horizontally. The patient and table are disposed between an x-ray source 14 and an x-ray detection means 16. The x-ray source propagates radiation through the patient and the patient table. The x-rays passing through the patient are selectively attenuated by various anatomical structures within the patient. Upon exiting the patient the x-rays contain two dimensional radiographic information regarding the patient. The exiting x-rays are directed onto an x-ray detection means 16 which converts the radiographic image into a two dimensional light image thereof.

Figure 2:
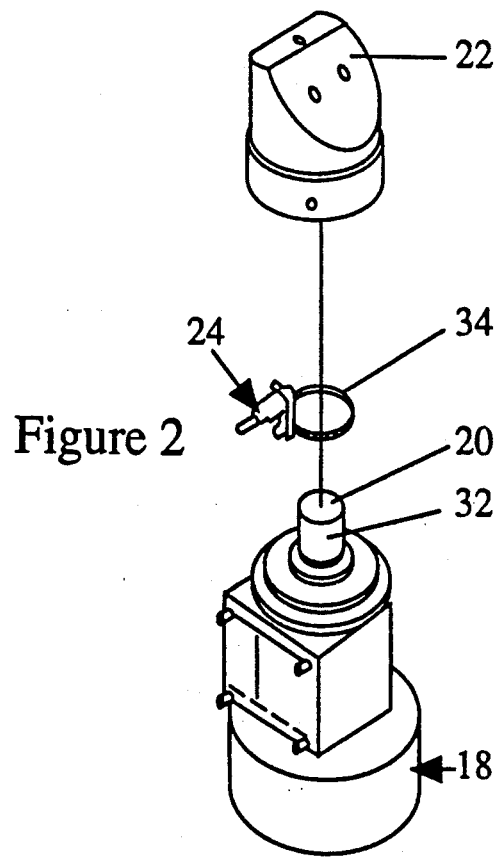
FIG. 2 is a partially exploded view of the intensifier tube, camera/intensifier tube holding means and the solid state sensor with adjustable viewing means.

With reference to FIG. 2 and continuing reference to FIG. 1, the x-ray detection means 16 is comprised of an evacuated intensifier tube 18. The input of intensifier tube is comprised of a fluorescent screen, which converts incident x-rays into a relatively low brightness visible light proportional to the intensity of the x-rays impinging at each point thereon. The fluorescent screen light is absorbed by an adjacent photo cathode within the intensifier tube. The photo cathode releases a quantity of relatively low energy electrons in proportion to the intensity of the visible light impinging at each point thereon. An electrical energy source applies a relatively high bias voltage between the photo cathode and intensifier tube output screen 20. The bias voltage accelerates the free electrons towards the output screen while a plurality of electrodes within the intensifier tube steers the electrons towards the output screen, which is typically smaller than the input screen. The accelerated electrons converge on and strike the output screen and are absorbed thereby. The absorption of the accelerated electrons by the output screen converts the electrons kinetic energy into a relatively bright flash of light. The light pattern at the intensifier tube output is a reduced sized bright light image of the radiographic image information present at the input thereof. A holding means 22 secures a video camera in position to directly or indirectly receive light output from the intensifier tube output screen. The video camera transfers the viewed image to a closed circuit television for direct diagnostic viewing.

Figure 3:
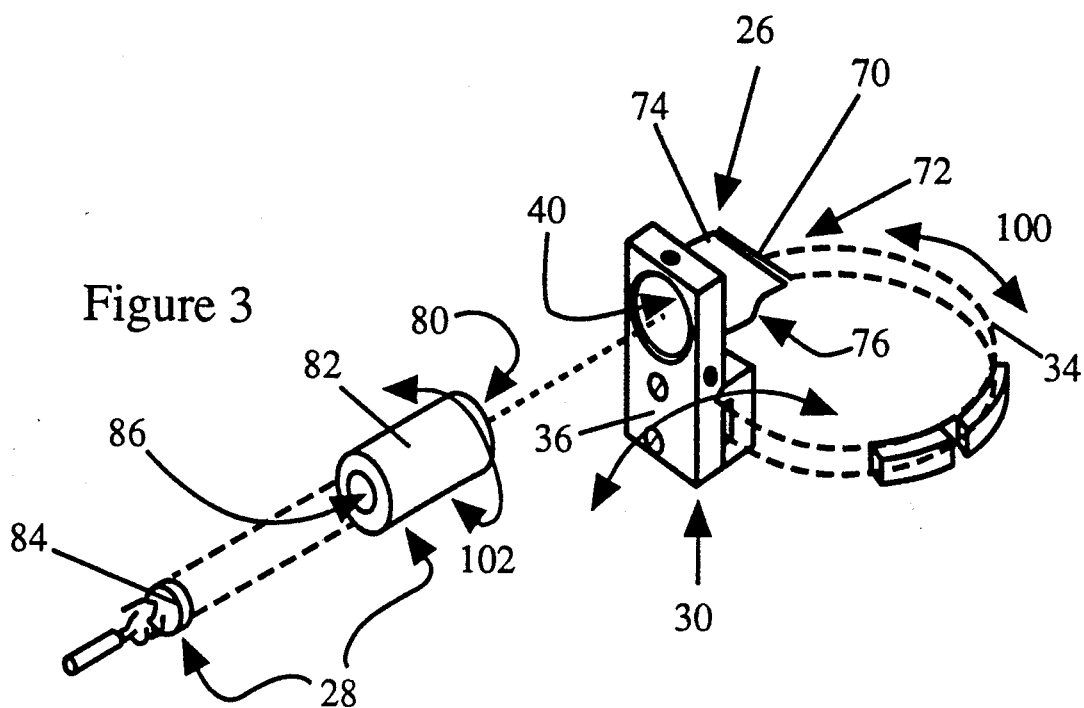
FIG. 3 is an exploded perspective view of the solid state sensor with adjustable viewing means.
Figure 4:
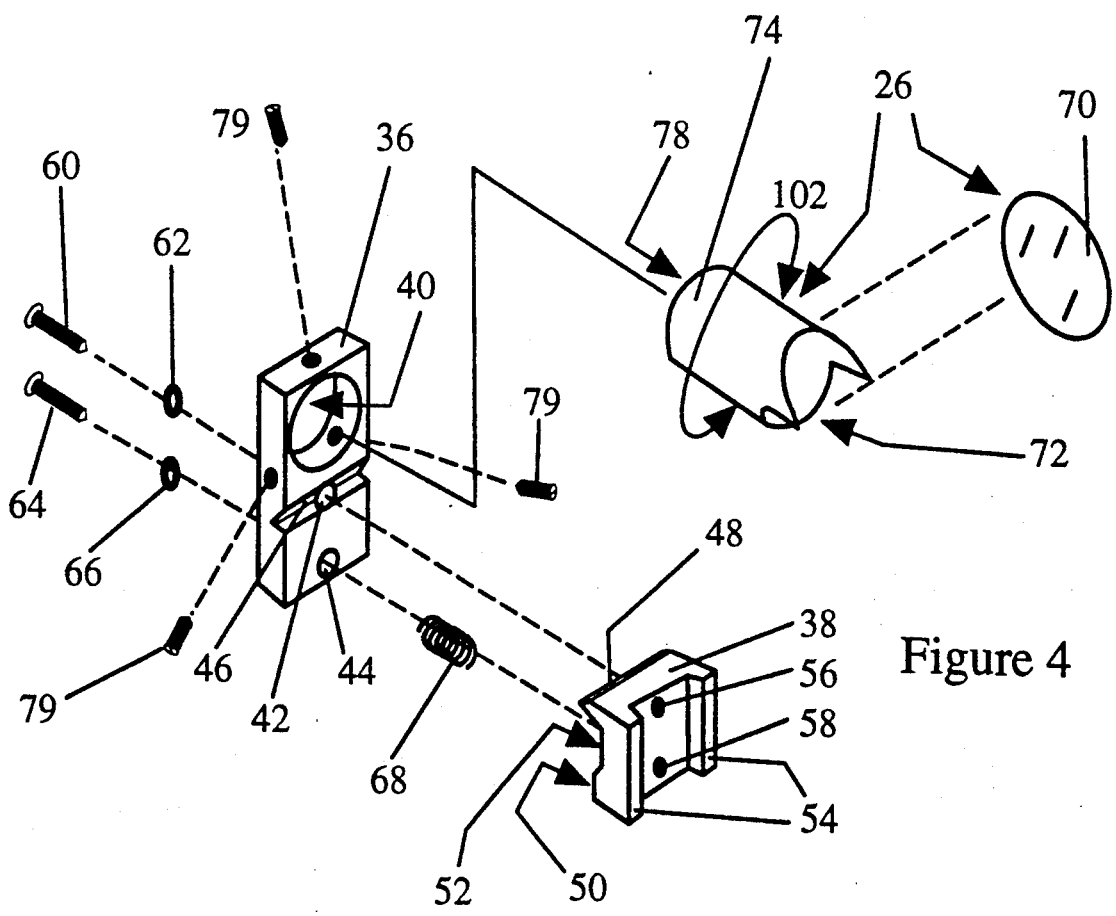
FIG. 4 is an exploded perspective view of the components for the adjustable viewing means.

With reference to FIGS. 3 and 4 and continuing reference FIG. 2, a sampling means 24 is provided. The sampling means includes a light directing assembly 26, a light receiving assembly 28 secured in optical alignment with the light directing assembly, an adjustment assembly 30 secured to the intensifier tube output neck 32 by a securing means 34, the adjustment supporting the light directing and light receiving assemblies such that the light receiving assembly can be adjusted to view light propagating from select one of a plurality of locations of the intensifier output screen 20.

Specifically, the adjustment assembly 30 is comprised of a first block 36 and a second block 38. The first block includes three holes in vertical alignment along the central vertical axis of the block. Upper most hole 40 is sized to frictionally receive the light directing assembly. The middle hole 42 and lower hole 44 are unthreaded clearance holes sized to receive screws therethrough. A shallow horizontal groove 46 is disposed midway on one side of the first block with the middle clearance hole disposed centrally therethrough.

The second block 38 is comprised of three portions on one side thereof. The first portion 48, disposed along the upper portion of one side of the second block, is a horizontal knife edge pivot. A second portion So, disposed along the bottom portion of the second block, is a generally flat rectangular surface extending along the width of the block. The knife edge pivot and the bottom rectangular portion form a clearance space 52 therebetween which is described more fully below.

The opposite side of second block 38 includes standoffs 54 on both vertical edges thereof. Upper and lower threaded screw holes 56 and 58 are disposed in vertical alignment along the central vertical axis of the second block. The upper threaded screw hole projects through the central portion of knife edge pivot and the lower threaded screw hole extends through the central part of the second portion. When the first and second blocks are assembled the knife edge pivot rests in groove 46, clearance hole 42 is aligned with threaded screw hole 56 and clearance hole 44 is aligned with threaded screw hole 58. A first screw 60 is projected through a washer 62, clearance hole 42 and is secured into threaded screw hole 56 securing the knife edge pivot to the groove. A second screw 64 is projected through a washer 66, clearance hole 44, a coil spring 68, and into threaded screw hole 58. The knife edge pivot and grove form a see-saw pivot thereabout. The lower portions of the first and second blocks are held in pivotal tension by the spring and the screw therethrough and create the adjustment means for the see-saw pivot. The height of the second block is such that it does not interfere with upper hole of the first block when assembled. Tightening or loosening of screw 64 provides pivotal adjustment of block 36 in relation to block 38.

The light directing assembly is comprised of mirror 70 secured at a select angle to one end 72 of first barrel 74. The end 72 has a cut-out 76 defined therein such that the mirror 70 can be disposed thereon to receive light propagating perpendicular to the central axis of the barrel without interference from the barrel. The second end 78 of the first barrel is frictionally secured in hole 40. Set screws 79 are disposed around the periphery of hole 40 and are used to secure the first barrel in hole 40 in the manner to be hereinafter described.

The light receiving assembly includes a first end 80 of a second barrel 82 frictionally engaged within the second end of the first barrel. The light receiving end of a photo diode 84 is frictionally engaged in a second end 86 of the second barrel. When combined in the above described manner the barrels hold the mirror and the photo diode light receiving end in fixed optical alignment such that light reflected by the mirror will always impinge on the photo diode regardless of the motion of the photo diode or the mirror.

The sampling means is secured to the intensifier output neck 32 by a band 34 routed through clearance space S2. The vertical standoffs 54 rest against the intensifier output neck, parallel to the central axis of the intensifier tube, and prevent the sampling means from rocking thereon while allowing rotation 100 of the sampling means about the intensifier output neck. The sampling means holds the central axis of the barrels generally perpendicular to the face of the image intensifier output screen. The barrels are positioned such that the reflective portion of the mirror is generally oriented to view light from the output screen and reflect the light to the photo diode. The photo diode output is operably connected to a control means which monitors the intensity of the light impinging thereon and dynamically adjusts the x-ray exposure in response.

Figure 5:
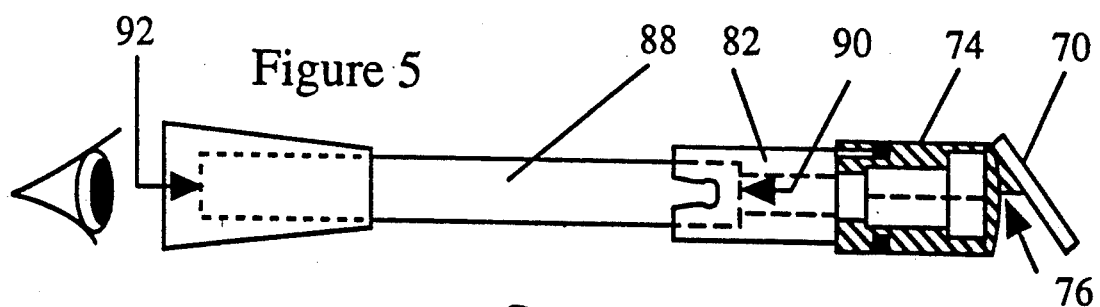
FIG. 5 is a isolation view of the observation apparatus frictionally engaged in the barrel apparatus of the solid state photo sensor with viewing means, one portion of the adjustable viewing means barrel shown in cross section.

With reference to FIG. 5 and continuing reference to all previous FIGS., the sampling means is adjusted to detect light propagating from a select portion of the intensifier output screen as follows. An small x-ray opaque marker is secured between the x-ray source and the intensifier tube preferably, adjacent the intensifier tube input screen and central thereto. The marker can be a simple metallic washer, machine screw or other more complex device. The photo diode 84 is temporarily removed from the second end 86 of the second barrel. A cylindrical observation apparatus 88, such as a microscope, having a first and second end is provided. The first end 90 of the microscope is frictionally engaged int he second end 86 of the second barrel such that the mirror 70 reflects an image of the intensifier tube output face through the central portion of the microscope to the second end 92 thereof. The x-ray source is engaged causing x-ray radiation to be propagated towards the face of the intensifier input screen. The marker attenuates X-ray radiation incident thereon producing a radiation shadow on the portion of the intensifier input screen adjacent the marker. The intensifier tube converts radiation impinging thereon into a relatively bright light image on the intensifier output screen face. Attenuated radiation causes little or no light to be generated by the intensifier tube at the portion of the tube adjacent the marker. Thus, the attenuated radiation manifests itself as a dark light portion on the intensifier output screen. For the purpose of this example it will be assumed that the dark light portion is a relatively small dark circle centered on the brightened output face however, it should be appreciated that other patterns of different sizes at different locations may also be useful.

while viewing the output screen reflection through the second end of the microscope the spring loaded screw 64 is adjusted pivoting the first block about the see-saw pivot. The screw adjustment causes the observation apparatus and mirror to be selectively aimed along a first imaginary line, generally perpendicular to the see-saw pivot axis, across the face of the intensifier output screen. The adjustment progresses until the dark circle is centered in the reflected image within the range of adjustment provided by the see-saw pivot. Next, while continuing to view the reflection of the output screen, the microscope and barrels are rotated 102 about the central axis thereof until the dark circle is centered within the reflected image. The rotational adjustment of the barrels results in the mirror being selectively aimed along a second imaginary line, generally perpendicular to the first line, across the face of the intensifier output screen. The intersection of the first and second lines defines the location of the dark circle as viewed by the mirror. The microscope is then removed from the second end 86 of the second barrel and the photo diode 84 is reinstalled. It should be appreciated that if the dark circle is centered in the viewing end of the microscope for either the range of pivotal and/or rotational adjustment it may not be necessary to make one or both adjustments as part of the adjustment process.

Alternatively, the sampling mean scan be adjusted as follows. With the photo diode operatively engaged in the second end 86 of the second barrel an electrical measuring device is connected to the photo diode 84 output, for measuring the electrical output in response to light impinging thereon. As above, a small x-ray opaque marker secured between the x-ray source and the intensifier tube results in a small dark circle appearing on the otherwise bright output screen of the intensifier tube when the x-ray source is engaged. While monitoring the photo diode electrical output, spring loaded screw 64 is adjusted pivoting the first block about the see-saw pivot until the electrical output is optimized for the range of motion provided thereby. Next, while continuing to monitor the electrical output of the photo diode, the barrels are rotated 102 about the central axis thereof until the photo diode output is optimized for the rotational adjustment of the barrels. Adjustment of the screw 64 and/or rotation of the barrels continues iteratively until the photo diode output is optimized for the range of motion provided by each adjustment means; this being an indication that the mirror is optimally aimed at the dark spot. The electrical measuring device is then disconnected from the photo diode output.

The spring and screw 64 arrangement holds blocks (36, 38) in their adjusted positions after adjustments are complete. Likewise, the friction between barrel 74 and hole 40 holds the barrel in its adjustment position after the adjustments are complete. Because the blocks and the barrel remain in their respective adjusted positions subsequent adjustments of either can progress therefrom such that the final adjustment of the mirror to the dark spot can progressively build upon prior adjustments. When rotational adjustment is complete the set screws 79 are tightened into the body of the first barrel to prevent subsequent rotation thereof.

It should be appreciated that the first and second barrels could be replaced by a single barrel that would hold the mirror and photo diode in an optical alignment as described above. It should also be appreciated that the focal length between the output face of the intensifier tube and the input of the photo diode could be adjusted by changing the total length of the barrels or by securing a focal lens in the first end 72 of the first barrel.

The above invention has been described with reference to the preferred embodiments. Obvious modifications and alterations will occur to other upon reading the preceding detailed description. It is intended that the invention be construed as including all such modifications and alterations insofar as the come within the scope of the appended claims or the equivalents hereof.

Having described the preferred embodiment the invention is now claimed to be:

1. An x-ray system including a source of x-ray radiation, an image intensifier tube having a input screen and an output screen, the input screen disposed to receive radiation from the x-ray source, the x-ray source and input screen defining a gap therebetween for disposing an object under examination, the output screen having a visible light image on a face thereof in response to radiation received by the input screen, a viewing means aligned to view the image present at the output screen and a light sampling means disposed between the output screen and the viewing means for sampling a portion of the output screen light, the light sampling means, comprising:
   a light directing means;
   a light receiving means;

an optical alignment means for fixing the light directing means and light receiving means in fixed optical alignment; and a adjustment assembly adjustably engaged to the optical alignment means such that the light directing means can be aimed to sample light propagating from a select one of a plurality of locations on the output screen while maintaining fixed optical alignment with the light receiving means.

2. The apparatus as set forth in claim 1 wherein the adjustment assembly includes means for progressively adjusting the aim of the optical alignment means.

3. The apparatus as set forth in claim 2 wherein the progressive aiming means of the adjustment assembly includes a means for rotatably engaging the optical alignment means such that the light directing means is rotatably adjustable to detect light propagating from a select one of a plurality of position lying on a line across the face of the output screen.

4. The apparatus as set forth in claim 2 wherein the adjustment assembly further includes a means for pivotally engaging the adjustment assembly such that the light directing means is pivotally adjustable to detect light propagating from a select one of a plurality of locations lying on a line across the face of the output screen.

5. The apparatus as set forth in claim 2 wherein the adjustment assembly further includes:

a means for rotatably engaging the optical alignment means such that the light directing means can be rotatably aimed to detect light propagating from a select one of a plurality of locations lying along a first line across the face of the output screen; and a means for pivotally engaging the adjustment assembly such that the light detecting means pivotally adjustable to detect light propagating from a select one of a plurality of locations lying along a second line across the face of the output screen, wherein the first and second lines are substantially perpendicular to one another and the intersection thereof defines the location where the sampling means views the output screen.

6. An X-ray system including a support means for supporting an object under examination, an x-ray source for propagating radiation along a path through the support means, an image intensifier tube having an input face and an output face, said input face receiving radiation passing through the support means and said output face defining a plane and producing a visible light image thereon of the radiation received at the input face and a sampling means for sampling a portion of the visible image produced at the output face, said sampling means comprising:

a light directing means including a mirror for reflecting the sampled light portion from the output face along a line generally parallel to the plane of the output face;

a light receiving means including a photo diode for producing an electrical signal representative of the sampled light portion;

an optical alignment means for securing the light directing means and light receiving means in optical alignment;

an adjusting means for adjusting the position of the optical alignment means in relation to the plane of the output face, said adjusting means further comprising:

means for pivoting the optical alignment means about an axis perpendicular to the line of reflected light defined by the optical alignment between the light directing means and light receiving means;

means for rotating the light directing means and light receiving means about the axis defined by the optical alignment between the light directing means and light receiving means;

7. An x-ray system including a source of x-ray radiation, an image intensifier tube having an input screen, an output screen and an output neck supporting the output screen, the input screen disposed to receive radiation from the x-ray source, the input screen and x-ray source defining a gap therebetween for disposing an object under examination, the output screen producing a visible light image in response to radiation received at the input screen, a viewing means aligned to view the image present at the output screen and a light sampling means disposed between the output screen and the viewing means for sampling a portion of the light from the output screen, the light sampling means, comprising:

a first block having a receiving aperture through an upper face portion and a shallow horizontal groove between the receiving aperture and the bottom portion of the block;

a second block having a horizontal knife edge pivot along an upper edge of a face thereof, an extending portion along the lower edge, the pivot and extending portion defining a clearance space therebetween;

the first block and the second block operatively coupled such that the knife edge pivot and the groove are in pivoting contact;

an adjustable biasing means disposed between the blocks and below the knife edge pivot for adjustably biasing the blocks in pivoting tension about the knife edge pivot;

an optical alignment means frictionally engaged in the receiving aperture, the optical alignment means having a first end and a second end;

a light receiving means secured to the first end of the optical alignment means;

a light reflecting means secured to the second end of the optical alignment means, the optical alignment means operatively coupling the light reflecting and light receiving means in fixed optical alignment;

the receiving aperture and optical alignment means cooperating to provide rotatable adjustment of the light receiving means about the axis defined by the optical alignment between the light reflecting means and the light receiving means;

the receiving aperture, optical alignment means and knife edge pivot cooperating to provide pivoting adjustment of the light receiving means about the knife edge pivot.

a securing band disposed through the second block clearance and around the output neck of the intensifier tube for securing the light sampling means to the intensifier tube such that the light receiving means is disposed between the face of the output screen and the viewing means for sampling a portion of the light from the output screen and reflecting the sampled light portion to the receiving means.

8. The apparatus as set forth in claim 7 wherein the receiving aperture is a hole and the optical alignment means is a barrel.

9. The apparatus as set forth in claim 7 wherein the receiving aperture is a hole and the optical alignment means is a plurality of barrels, a first barrel frictionally and rotatably engaged in the receiving aperture, subsequent barrels frictionally engaged in the first barrel such that the central axis of the barrels are coextensive.

* * * * *